United States Patent [19]

Nagao et al.

[11] 4,128,762

[45] Dec. 5, 1978

[54] APPARATUS FOR MEASURING MECHANICAL STRESS USING WHITE X-RAYS

[75] Inventors: Masato Nagao; Sho Kusumoto, both of Hitachi, Japan

[73] Assignee: Hitachi, Ltd., Japan

[21] Appl. No.: 813,299

[22] Filed: Jul. 6, 1977

[30] Foreign Application Priority Data

Sep. 8, 1976 [JP] Japan .............................. 51-106723

[51] Int. Cl.$^2$ ........................................... G01N 23/20
[52] U.S. Cl. .................................... 250/272; 250/274
[58] Field of Search ......... 250/272, 273, 274, 277 CH

[56] References Cited

U.S. PATENT DOCUMENTS 3,617,705 11/1971 Takano .................................. 250/273
3,934,138 1/1976 Bens ..................................... 250/272

Primary Examiner—Craig E. Church
Attorney, Agent, or Firm—Craig & Antonelli

[57] ABSTRACT

An apparatus for measuring mechanical stress in one direction (along the x-axis) in the surface of a sample, using white X-rays, wherein white X-rays are cast onto the surface of the sample from on one side of the plane (z-x plane) containing the white X-rays cast position on the surface of the sample, being perpendicular to the surface (x-y plane) of the sample and extending in the direction (along x-axis) along which the stress is measured; the energy of the X-rays diffracted by the lattice planes parallel to the surface of the sample, is detected at a predetermined Bragg angle while the energy of the X-rays diffracted by the lattice planes whose normals are contained in the z-x plane and which incline at an angle with respect to the surface of the sample, is detected also at the same Bragg angle; and the stress $\sigma_x$ in the x-axis direction in the sample surface is calculated on the basis of the difference between the two energies according to the expression $$\sigma_x = K \frac{E_{n1} - E_{n2}}{\sin^2 \psi_2},$$

where $E_{n1}$ is the energy of the X-rays diffracted by the lattice planes parallel to the sample surface, $\overline{E}_{n2}$ the energy of the X-rays diffracted by the lattice planes including at an angle to the sample surface, $\psi_2$ the angle which is made by the normal to the sample plane and the normal to the inclining lattice planes, and K is a constant given by the expression $$K = - \frac{E}{1 + v} \frac{1}{\overline{E}_n},$$

where E is the Young's modulus, $v$ the Poisson's ratio, and $E_n$ the energy of the X-rays diffracted by the sample when it has no strain therein.

9 Claims, 5 Drawing Figures

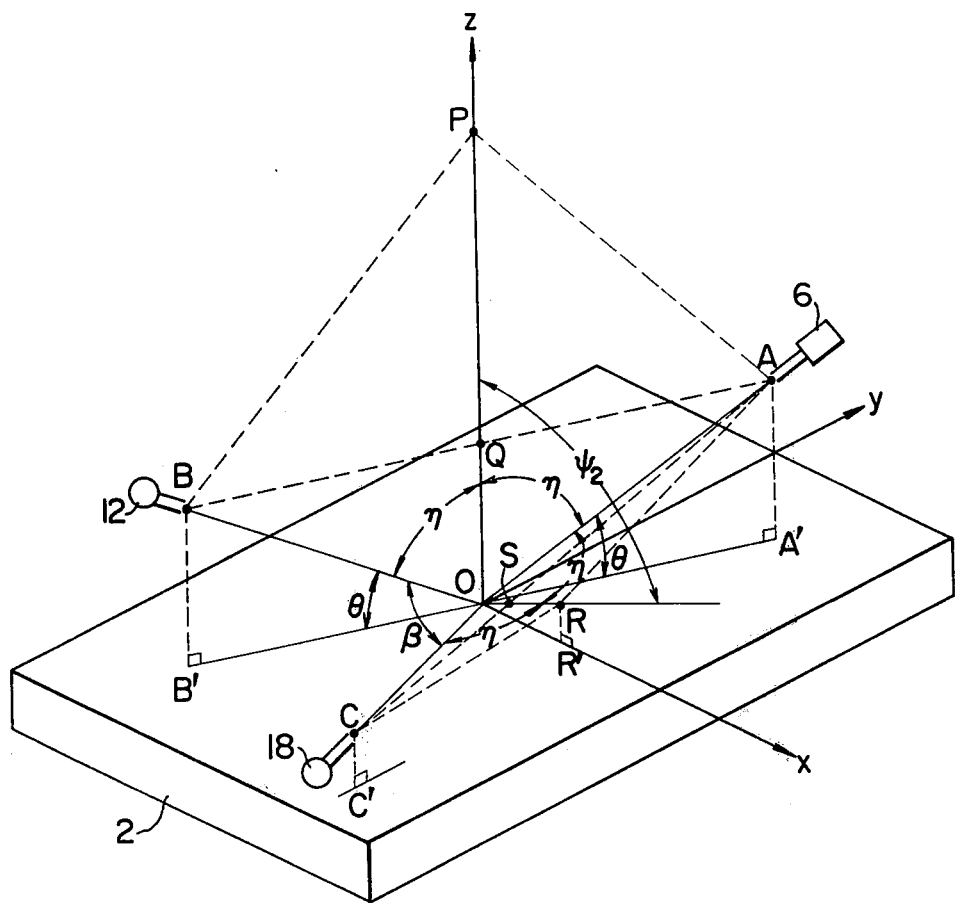
F I G. 3

APPARATUS FOR MEASURING MECHANICAL STRESS USING WHITE X-RAYS

The present invention relates to an apparatus for measuring the mechanical stress in the surface of a sample, using white X-rays and especially using the three-dimensional location of an X-ray source and two X-ray detectors and of two X-ray sources and an X-ray detector.

The object to be measured is polycrystalline. When X-rays impinges upon a crystal, the diffracted components are obtained from the crystal if the Bragg condition is satisfied such that $$\lambda = 2d \sin\theta \quad (1),$$

where $\lambda$ is the wavelength of the incident X-rays, $d$ the distance between the juxtaposed lattice planes, and $\theta$ the Bragg angle.

The conventional stress measurement methods using X-rays are based on the characteristic X-ray diffraction method. According to the method, characteristic X-rays from a source are projected, along a plane perpendicular to the surface of a sample, onto the sample surface and by making X-ray detectors go round the sample in the perpendicular plane, the graph showing the relationship between the Bragg angle and the intensity of the diffracted X-rays is drawn to obtain the specific Bragg angle corresponding to the peak of the intensity. Then, the lattice spacing $d$ is calculated according to the above expression (1).

On the other hand, the mechanics of elasticity teach the following expression (2) representing the relationship between the stress $\sigma_x$ in the direction of one of the surfaces of a sample (i.e. x-axis direction) and the strain $\epsilon_\psi$ in the direction inclining at an angle $\psi$ toward the x-axis direction from the normal to the sample, which normal is contained in the z-x plane.

$$\sigma_x = \frac{E}{1+\nu} \frac{\delta\epsilon_\psi}{\delta\sin^2\psi} \quad (2),$$

where E is the Young's modulus and $\nu$ is the Poisson's ratio. This expression (2), however, is obtained under the condition that there is no stress $\sigma_z$ in the direction along the normal to the sample (i.e. z-axis direction).

The strain $\epsilon_\psi$ can be expressed as follows:

$$\epsilon_\psi = d_\psi - d_o/d_o \quad (3),$$

where $d_o$ is the lattice spacing of the lattice planes having arbitrary direction and no strain, and $d_\psi$ the lattice spacing of the lattice planes whose normal inclines at an angle $\psi$ toward the x-axis from the z-axis and which are affected by strain.

As described above, by swinging the X-ray detector around the sample, the lattice spacings $d_o$ and $d_\psi$ can be obtained according to the expression (1) above. The substitution of the thus obtained lattice spacings $d_o$ and $d_\psi$ into the expression (3) yields $\epsilon_\psi$, for which the stress $\sigma_x$ in the direction of x-axis can be calculated from the expression (2).

According to the characteristic X-ray diffraction method described above, there is a need for mechanical swing or scan of the X-ray detector and therefore unless the correspondence between the speed of scanning the X-ray detector and the rate meter is kept in a good condition, the plotted profile of the diffracted X-rays may deviate from the genuine one. For this reason, the scanning speed of the detector cannot exceed a certain limit. To overcome this weakpoint, there has been proposed a measurement method using two detectors for the purpose of halving the scanning time. However, this method still consumes too much time for measurement. Further, according to this method, elaborate steps must be taken since there is a need for calculation of the spacings $d_o$ and $d_\psi$ of the lattice planes respectively without and with strains.

Among other stress measurement apparatus using X-rays is one based on the white X-ray diffraction method. This apparatus has been invented by Masato Nagao, one of the Inventors of the present apparatus, and disclosed in the Japanese Patent Application Kokai (Laid-Open) No. 147983/75. According to the white X-ray diffraction stress measurement apparatus, the wavelengths of the diffracted X-rays are measured while the Bragg angle $\theta$ is kept constant, so that the mechanical scanning of the X-ray detector is not needed. Consequently, the apparatus has an advantage of rapidly measuring stress.

When white X-rays are cast onto the surface of a sample having numberless lattice planes directed at random, the X-rays having a single wavelength are detected by the X-ray detector fixed at a certain position in space. By obtaining the energy $E_n$ of the detected X-rays by a multi-channel pulse height analyzer coupled to the detector, the wavelength $\lambda$ can be calculated according to the expression (4) below.

$$\lambda = hc/E_n = 12.398/E_n \quad (4),$$

where $h$ is the Planck's constant and $c$ the velocity of light.

It follows from (1) and (4) that $$d = 6.199/E_n \sin\theta \quad (5)$$

The differentiation of the expression (5) with respect to $E_n$ yields $$\Delta d = - 6.199/E_n^2 \sin\theta \, \Delta E_n \quad (6)$$

By canceling $\sin\theta$ from the expressions (5) and (6), there is obtained the following equation.

$$\Delta d/d = - \Delta E/E_n \quad (7)$$

If $d$ in the left hand side of the equation (7) is regarded as the lattice spacing $d_o$ in the absence of strain, the term $\Delta d/d_o$ represents strain. It follows, therefore, from (3) and (7) that $$\epsilon_\psi = - \frac{\Delta E_n}{\overline{E_n}} \quad (8),$$

where $\overline{E_n}$ is the energy of the X-rays diffracted from the sample without strain. The substitution of (8) for (2) results in $$\sigma_x = - \frac{E}{1+\nu} \frac{1}{\overline{E_n}} \frac{\delta E_n}{\delta\sin^2\psi} \quad (9)$$

By putting $$K = -\frac{E}{1+\nu}\frac{1}{\overline{E_n}} \quad (10),$$

the expression (9) can be reduced to $$\sigma_x = K\frac{\delta E_n}{\delta \sin^2\psi} \quad (11)$$

The expression (11) means that $\sigma_x$ equals the slope of a curve plotted according to the relationships between $\sin^2\psi$ and $E_n$. In this case, $\psi$, which is the angle of inclination from the z-axis in the z-x plane, is varied while the Bragg angle $\theta$ is kept constant and the energy $E_n$ is measured for various values of $\psi$. Incidentally, if the sample is fixed in a certain position, $\theta_x$ takes a constant value. In addition, K is a constant and then it is clear from (11) that $E_n$ is linearly related to $\sin^2\psi$. Therefore, if the values of $E_n$ are determined through measurement for two values of $\psi$, $\sigma_x$ can be specified. Now, provided that $\psi_1 = 0$ and $\psi_2 \neq 0$ and that the energies $E_{n1}$ and $E_{n2}$ correspond respectively to $\psi_1$ and $\psi_2$, then the expression (11) can be transformed into $$\sigma_x = K\frac{E_{n2} - E_{n1}}{\sin^2\psi_2} \quad (12)$$

Accordingly, by casting white X-rays upon the surface of a sample at an angle $\eta$ (complementary to Bragg angle $\theta$) with respect to the z-axis in the z-x plane, the energy $E_{n1}$ of the X-rays diffracted at the angle $\eta$ to the opposite side of the z-axis from the lattice planes parallel to the sample surface and the energy $E_{n2}$ of the X-rays diffracted at an angle $3\eta$ with respect to the z-axis from the lattice planes having their normals in the z-x plane and inclining at an angle $2\eta$ ($= \psi_2$) with respect to the z-axis, are both detected and the stress $\sigma_x$ in the x-axis direction can be obtained through substitution of $E_{n1}$, $E_{n2}$ and $\psi_2$ ($= 2\eta$) obtained above for (12).

Such an apparatus for measuring stress in a sample in two-dimensional manner is disclosed in the above-mentioned Japanese Patent Application Kokai (Laid-Open) No. 147983/75.

According to the stress measurement apparatus of the two-dimensional type, as seen from (9) and (12), there is no need for accurately obtaining the absolute values of the two energy peaks of the diffracted X-rays for different $\psi$ angles and the same Bragg angle, but the difference between the two energy peaks has only to be exactly obtained. In the expressions (9) and (12) is contained the energy $\overline{E_n}$ of the diffracted X-rays in the absence of strain. The energy $\overline{E_n}$ assumes a value depending on the spacing $d_o$ of the lattice planes in the absence of strain, which value is affected to a certain degree by the fluctuation of room temperature and the composition of the elements in an alloy, but since a similar influence exists even in the stress measurement method using characteristic X-rays, it never forms a factor for degrading the accuracy in measurement.

As seen from the expression (6), the accuracy in measurement may be raised by increasing the value of $\Delta E_n/\Delta d$ and it is therefore preferable to increase $E_n$ and hence to measure the diffracted X-rays having high energy levels. In order to increase the energy levels $E_n$ of the diffracted X-rays and therefore to shorten the wavelengths $\lambda$ of the diffracted X-rays, it is necessary to make the Bragg angle $\theta$ small, as seen from (1). The accuracy in measurement does not depend on the Bragg angle $\theta$, but on the energy of the diffracted X-rays. So, the smaller is the Bragg angle, the more intense are the diffracted X-rays and therefore the higher is the accuracy in measurement. In such a case, it is preferable to make the Bragg angle $\theta$ less than 40°. However, with the stress measurement apparatus of the two-dimensional type, the Bragg angle cannot be set less than 60° if the surface of the sample is a plane.

Further, as seen from (9), $E_n$ varies linearly as $\sin^2\psi$ and it is necessary to make $\psi$ large so that the energy levels of the X-rays to be detected may be heightened. Also in that case, however, the apparatus of the two-dimensional type can have $\psi$ larger than 30°.

The object of this invention is to provide a stress measurement apparatus using white X-rays, in which the stress in a sample is measured with the Bragg angle set at a small value.

According to this invention, in the case of stress measurement by the white X-ray diffraction method, the X-rays diffracted by the lattice planes having the same orientation as the surface of a sample and by the lattice planes inclining at an angle $\psi_2$ with respect to the sample surface toward the direction in which the stress is measured, can be detected during a short time by the combination of an X-ray source and two X-ray detectors or of an X-ray detector and two X-ray sources while the Bragg angles for the X-rays diffracted by the two kinds of lattice planes are set equal to each other. In order to improve the accuracy in measurement by making the Bragg angle small so that the energies of the diffracted X-rays may be increased, the X-ray souce and the two X-ray detectors or the X-ray detector and the two X-ray sources are disposed in three-dimensional arrangement in such a manner that the source is separated from the detectors or the detector is separated from the sources, by a plane containing the normal to the sample surface and the direction in which the stress is to be measured.

Other objects and features of this invention will become apparent when any one skilled in the art reads the following description of the embodiment of this invention taken in conjunction with the attached drawings.

FIG. 3 illustrates in a perspective view in further detail the principle of the apparatus embodying this invention than FIG. 2;

Figure 1:
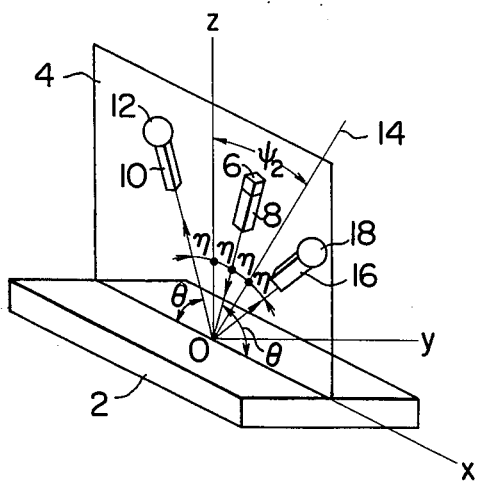
FIG. 1 illustrates the principle of the conventional stress measurement apparatus using white X-rays.

For a better understanding of this invention, the conventional stress measurement apparatus of two-dimensional type, using white X-rays will first be described with the aid of FIG. 1.

Let the surface of a sample 2 coincide with the x-y plane and a normal to the sample surface with the z-axis direction. It is now assumed that the stress $\sigma_x$ in the sample surface in the x-axis direction is to be measured. White X-rays emitted from an X-ray source 6 disposed in the z-x plane 4 perpendicular to the sample surface, i.e. x-y plane, are cast parallel to the z-x plane 4 and at an angle η (complementary to Bragg angle θ) with respect to the z-axis and concentrated through Soller slits 8 upon the origin O of the three-dimensional rectangular coordinate system (x, y, z). The incident X-rays are reflected by the lattice planes parallel to the sample surface. The diffracted X-rays make an angle η with the z-axis and detected by a first X-ray detector 12 through Soller slits 10. The detector 12 is connected with a multi-channel pulse height analyzer (not shown), which measures the energy $E_{n1}$ of the diffracted X-rays. The incident X-rays are also reflected by the lattice planes whose normals 14 lie in the z-x plane and make an angle $\psi_2$ with the z-axis. The diffracted X-rays make an angle 3η with the z-axis and are detected by a second X-ray detector 18 through Soller slits 16. The detector 18 is connected with another multi-channel pulse height analyzer not shown either, which measures the energy $E_{n2}$ of the X-rays detected by the detector 18. With this arrangement of the X-ray source 6 and the X-ray detectors 12 and 18, if the incident angle η is set equal to 30°, the detector 18 must lie on the x-axis. In the case where the sample surface is flat, therefore, the X-ray source 6 and detectors 12 and 18 must be so arranged that η may be less than 30°, that is, that the Bragg angle θ may be greater than 60°.

While the conventional apparatus employs the two-dimensional arrangement of the X-ray source and detectors, this invention adopts the spatial, i.e. three-dimensional, arrangement of them. An example of such a three-dimensional arrangement is shown in FIG. 2.

Figure 2:
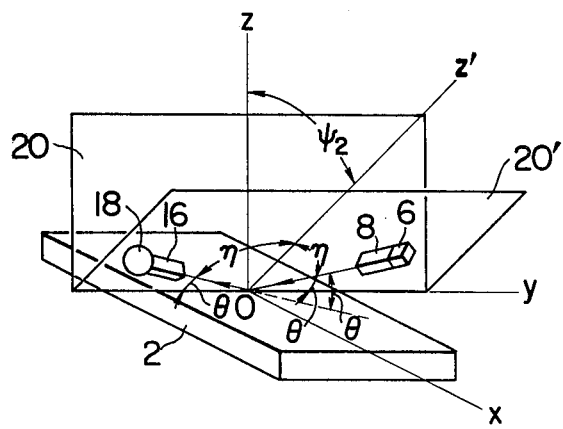
FIG. 2 illustrates the principle of the stress measurement apparatus using white X-rays, according to this invention.

In FIG. 2, the geometrical interrelation between the sample 2 and the (x,y,z) coordinate system is the same as in FIG. 1. Now, let the y-z plane 20 be introduced. The y-z plane 20 is then rotated about the y-axis through an angle $\psi_2$ positively and the slant y-z plane is denoted by a numeral 20'. White X-rays from the X-ray source 6 lying in the inclined plane 20' are cast parallel to the plane 20' and at an angle θ with the y-axis and directed through the Soller slits 8 to the predetermined origin O of the coordinate system (x,y,z) on the sample surface. The X-ray detector 18 is so disposed in the inclined plane 20' that the X-rays diffracted by the sample at the origin O, parallel to the plane 20' and at an angle θ with the negative portion of the y-axis, may be detected through the Soller slits 16. Let the line of intersection of the slant plane 20' and the z-x plane be defined as z'-axis. Then, the X-rays detected by the detector 18 are those reflected from the lattice planes whose normals are parallel to the z'-axis, that is, whose normals are parallel to the z-x plane and which cut the sample surface at an angle $\psi_2$. The angle $\psi_2$ is that which appears in the expression (12) so that the energy of the X-rays detected by the X-ray detector 18 equals $E_{n2}$ given by the expression (12). The X-rays reflected by lattice planes parallel to the sample surface are detected by an X-ray detector 12 (not shown) disposed at the rear of the y-z plane 20. It should here be noted that the X-rays emitted from the source 6 toward the sample surface have to make an angle θ with the x-y plane as well as the y-axis and also that the detector 12 (not shown) has to be so arranged as to receive the X-rays diffracted from the sample at an angle θ with the sample plane.

As described above, according to this invention, any Bragg angle θ in the range of 0°–90° can be selected so that the Bragg angle smaller than 40°, which is very preferable for measurement, can be easily set. Further, the angle ψ between the normal to the sample surface and the normal to a slant lattice plane increases with the decrease in θ and therefore a high precision in measurement can be attained.

In order to compensate for the errors caused in setting the Bragg angle θ and the angle ψ between the normals to sample surface and lattice plane, the three-dimensional type stress measurement apparatus has to be provided with Soller slits. In the diffraction system using Soller slits, the optical resolution, i.e. angle of divergence, of X-rays depends upon the directivity of the Soller slits but hardly upon the spot size of the Z-rays at focus. Therefore, according to the three-dimensional X-ray diffraction method using Soller slits, the cross sectional area of the X-ray beam can be of moderate size and therefore X-rays having high intensity can be used. The advantage in the capability of using highly intense X-rays is that comparatively intense X-rays can be detected after diffraction even if there is an error in positioning the sample. The Soller slits also make possible the use of detectors having large windows so that there is further compensated an error in positioning the sample.

While FIG. 2 shows a three-dimensional arrangement as an embodiment of this invention, FIG. 3 shows a three-dimensional geometry for more detailed description, according to this invention.

FIG. 3 shows the optical arrangement of an X-ray source and X-ray detectors relative to a sample, employed in a stress measurement apparatus according to this invention, in which stress is rapidly measured by using the optical system in a three-dimensional mode with Bragg angle θ kept constant and by simultaneously detecting by a combination of an X-ray source and two X-ray detector the X-rays diffracted from lattice planes parallel to the sample surface and the X-rays diffracted from lattice planes inclining at an angle $\psi_2$ with the sample surface.

In FIG. 3, the position at which an X-ray source 6 emits X-rays is indicated by reference letter A; the windows of detectors are located at the positions B and C; positions P and Q lie on a normal to the surface of a sample; the points A' and B' are the projections of the points A and B onto the sample surface; and the stress in the sample surface is measured at the position indicated by O. The points P, B, B', O, A', A and Q lie on a plane (containing the normal to the sample surface at O). The X-rays diffracted from the lattice planes parallel to the sample surface are measured by casting X-rays in the direction A-O-B. The points R and S lie on a straight line contained in the z-x plane and making an angle $\psi_2$ with the z-axis and the point R' is the projection of point R onto the sample surface. The points A, O, C, R and S lie on a plane. The X-rays diffracted from lattice planes whose normals are parallel to the straight line $\overline{OR}$, are measured by casting X-rays in the direction A-O-C. In addition, the x-axis is the direction in which stress $\sigma_x$ in the sample is measured, the point O is the position upon which the X-rays are cast (at which the stress is to be measured), and the angle η is complementary to Bragg angle θ. The bisector OQP for the angle AOB is so arranged as to concide with the z-axis. The window C of the detector 18 is so arranged that ∠AOB = ∠AOC and that the straight line OC makes an angle β with the straight line OB. If the projection of the bisector OSR for the angle AOC upon the sample surface is set coincident with the x-axis (here, the bisector OSR is parallel to the normals to the lattice planes from which the X-rays detected by the detector 18 are diffracted), the normal OQP to the lattice planes from which the X-rays detected by the detector 12 are diffracted, becomes parallel to the normal to the sample surface. Accordingly, with this arrangement, the normals to the two kinds of the lattice planes make angles of O and $\psi_2$ respectively with the normal to the sample surface so that the detectors 12 and 18 can simultaneously detect the X-rays diffracted by the two kinds of the lattice planes. The angle $\psi_2$ can be expressed in terms of the angle $\beta$ and the Bragg angle $\theta$ such that $$\cos\psi_2 = 1 - \frac{1 - \cos\beta}{4 \sin^2\theta} \quad (13),$$

where $\theta = \pi/2 - \eta$.

According to this method described above, the X-rays diffracted from the two kinds of the lattice planes can be detected simultaneously while the Bragg angle $\theta$ is kept small, as is the preferable condition for the white X-ray diffraction method.

If the Bragg angle $\theta$ is assumed here to be 30°, it follows from the expression (13) that $$\psi_2 = \beta \quad (14)$$

As a result, the angle $\psi_2$ can be precisely determined in the measurement of stress. To select the condition that $\theta = 30°$ or $\eta = 60°$, $\theta$ being sufficiently small, preferably results in high precision in measurement and also facilitate the derivation of stress through calculation.

Moreover, the angle $\theta$ equal to 30° is so small even for the white X-ray diffraction method that the diffracted X-rays can be easily detected.

The angle $\beta$ or $\psi_2$ can be arbitrarily chosen, but when it equals 60°, the detector 18 has to be brought too near to the sample surface and therefore it is preferable to chose it to be 45°.

The foregoing description of the embodiment of this invention has been given to the case where one X-ray source and two X-ray detectors are used in combination. It is clear to thsoe skilled in the art, however, that the roles of the above X-ray source and detectors can be interchanged, that is, two X-ray sources can be substitute for the detectros 12 and 18 while one X-ray detector can replace the source 6. In that case, since the detector detects energy peaks at different positions, the X-ray signals diffracted from the two kinds of lattice planes can be separated from each other. The X-ray signals can also be separated from each other by the time sharing process.

Figure 4:
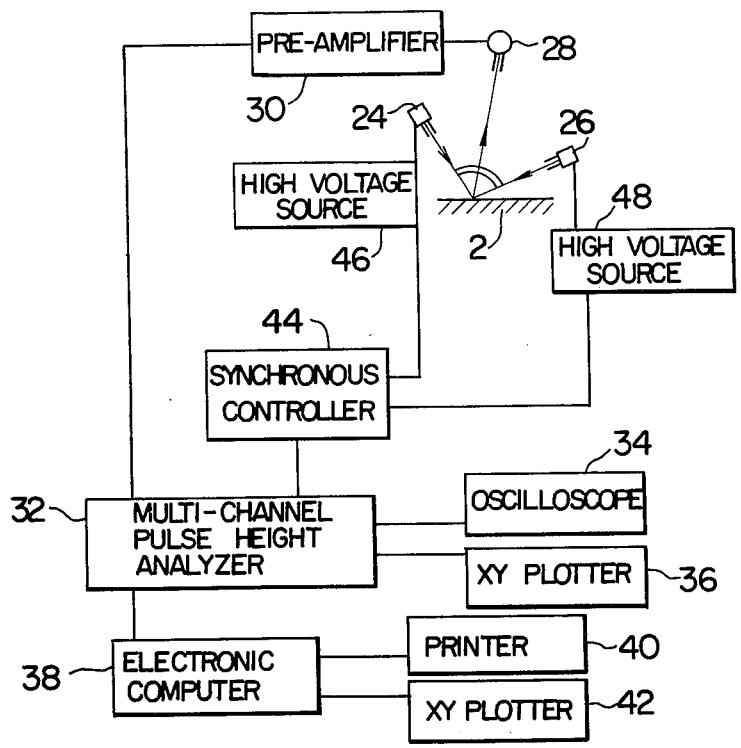
FIG. 4 shows in block diagram an example of a signal processing system used with this invention.

FIG. 4 schematically shows a method of analyzing X-ray energy, as an embodiment of this invention, using two X-ray sources and an X-ray detector with the Bragg angle $\theta$ kept the same.

Two X-ray sources 24 and 26 are used with an X-ray detector 28. The signal detected by the detector 28 is sent through a preamplifier 30 to a multi-channel pulse height analyzer 32, which analyzes the energy of the detected X-rays for the display of the diffraction pattern or profile on an oscilloscope 34 or an XY plotter 36. Also, the signal from the multi-channel pulse height analyzer 32 may be analyzed by an electronic computer 38 and the result of the analysis may be displayed on a printer 40 or an XY plotter 42.

A synchronous controller 44 sends signals respectively to high voltage sources 46 and 48 for the X-ray sources 24 and 26 to cause the X-ray sources to alternately emit white X-rays impinging upon the same position on the sample surface. The multi-channel pulse height analyzer 32 consists of two channel groups which alternately operate in synchronism with the operation of the synchronous controller 44. For example, in the case where a multi-channel pulse hight analyzer having two thousand channels is used, the channels #1 to #1000 may be used for the analysis of the signal corresponding to the diffracted versious of the X-rays emitted from the X-ray source 24 and the channels #1001 to #2000 for the analysis of the signal corresponding to the diffracted versious of the X-rays from the source 26. Also, the odd numbered channels may be allotted for the analysis of one signal and the even numbered ones for the analysis of the other.

Figure 5:
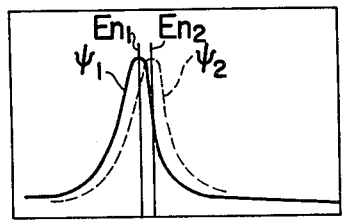
FIG. 5 graphically shows the shift of the peaks of the energies of the X-rays diffracted by two lattice planes having different angles of inclination.

FIG. 5 shows that the peaks of the energies $E_{n1}$ and $E_{n2}$ for angles $\psi_1$ and $\psi_2$ of inclination of the sample surface appear at different positions.

Although the absolute values of the energies $E_n$ can hardly be obtained within a range higher than $10^{-4}$ in accuracy (i.e. $\Delta E_e/E_n < 10^{-4}$, where $\Delta E_e$ is error) even if the energy calibration of the multi-channel pulse height analyzer is precisely performed, the difference between $E_{n1}$ and $E_{n2}$ can be easily obtained with high precision. It is a matter of course that the energy step at least in the vicinity of the point of diffraction under investigation can be obtained rather precisely if the energy calibration of the multi-channel pulse height analyzer is precisely performed according to the peak positions or peak shift of a reference sample.

In the white X-ray diffraction method, the higher the energy level of the used X-rays, the higher is the precision in measurement. It is difficult, however, to fabricate an X-ray tube capable of generating X-rays having a high energy and intensity for a long time. There is a risk of melting the target for reason of the generated heat so that the emitted X-rays are unstable. Therefore, the alternate actuation of the two X-ray sources as described above will increase the effect of cooling and is advantageous in obtaining X-rays having high energy. By causing the analyzer to accumulate count values in timing with the alternate actuation of the X-ray sources, the diffracted components of the X-rays from the two X-ray sources are almost simultaneously separated from each other, detected and analyzed separately.

What we claim is:

1. An apparatus for measuring mechanical stress, using white X-rays, comprising an X-ray source so disposed as to cast white X-rays upon a position in the surface of a sample where the stress is to be measured, said X-rays travelling along a first plane containing a normal to said position and obliquely crossing with a second plane which includes said normal and which extends in the direction in which the stress is measured, said X-rays impinging upon said position at an angle $\eta$ with said normal;

a first X-ray detector so disposed as to receive the X-rays diffracted from said position at said angle $\eta$ with said normal, said diffracted X-rays travelling along said first plane;

a second X-ray detector so disposed as to receive the X-rays diffracted from said position at said angle $\eta$ with a line existing in said second plane, making an angle $\psi_2$ with said normal, making the angle $\eta$ with the path of said white X-rays from said X-ray source and passing through said position in the sample surface, said diffracted X-rays travelling along a third plane containing said line and said path; and a multi-channel pulse height analyzer for analyzing the X-ray signals detected by said first and second X-ray detectors, wherein said stress $\sigma_x$ is obtained according to the following formula $$\sigma_x = K \frac{E_{n2} - E_{n1}}{\sin^2 \psi_2},$$

where $E_{n1}$ and $E_{n2}$ are the energies of X-rays detected respectively by said first and second X-ray detectors and K is a constant such that $$K = -\frac{E}{1+\nu} \frac{1}{\overline{E}_n},$$

where E is the Young's modulus, $\nu$ the Poisson's ratio, and $\overline{E}_n$ the energy of diffracted X-rays in the case where is no strain in said sample and where the Bragg angle is complementary to said angle $\eta$.

2. An apparatus as claimed in claim 1, wherein said angle $\eta$ is not less than 50°.

3. An apparatus as claimed in claim 2, wherein said angle $\eta$ is set equal to 60°.

4. An apparatus as claimed in claim 1, wherein Soller slits are provided for said X-ray source and detectors.

5. An apparatus for measuring mechanical stress, using white X-rays, comprising a first X-ray source so disposed as to cast white X-rays upon a position in the surface of a sample where the stress is to be measured, said X-rays travelling along a first plane containing a normal to said position and obliquely crossing with a second plane which includes said normal and which extends in the direction in which the stress is measured, said X-rays impinging upon said position at an angle $\eta$ with said normal;

an X-ray detector so disposed as to receive the X-rays diffracted from said position at said angle $\eta$ with said normal, said diffracted X-rays travelling along said first plane;

a second X-ray source so disposed as to cast white X-rays upon said position at said angle $\eta$ with a line existing in said second plane, making an angle $\psi_2$ with said normal, making the angle $\eta$ with the path of said diffracted X-rays and passing through said position in the sample surface, said white X-rays from said second X-ray source travelling along a third plane containing said line and said path; and a multi-channel pulse height analyzer for analyzing the two kinds of signals detected by said detector corresponding to said X-rays from said first and second sources, wherein said stress $\sigma_x$ is obtained according to the following formula $$\sigma_x = K \frac{E_{n2} - E_{n1}}{\sin^2 \psi_2},$$

where $E_{n1}$ and $E_{n2}$ are the energies of the diffracted X-rays which are respectively emitted from said first and second X-ray sources and K is a constant such that $$K = -\frac{E}{1+\nu} \frac{1}{\overline{E}_n},$$

where E is the Young's modulus, $\nu$ the Poisson's ratio, and $\overline{E}_n$ the energy of diffracted X-rays in the case where there is no strain in said sample and where the Bragg angle is complementary to said angle $\eta$.

6. An apparatus as claimed in claim 5, wherein said angle $\eta$ is not less than 50°.

7. An apparatus as claimed in claim 6, wherein said angle $\eta$ is set equal to 60°.

8. An apparatus as claimed in claim 5, wherein said apparatus further comprises a controller for alternately actuating said first and second X-ray sources so as to cause said sources to alternately cast white X-rays upon said position and wherein said multi-channel pulse height analyzer consists of two groups of channels, said two groups being alternately operated in synchronism with the operation of said controller.

9. An apparatus as claimed in claim 5, wherein Soller slits are provided for said X-ray sources and said X-ray detector.

* * * * *